United States Patent
Wang (10) Patent No.: US 9,408,807 B2
(45) Date of Patent: Aug. 9, 2016

(54) SEMI-PERMEABLE ENCAPSULATION SYSTEM WITH TAPERED CONDUITS FOR DIABETES REVERSAL

(71) Applicant: Taylor Gun-Jin Wang, Los Angeles, CA (US)

(72) Inventor: Taylor Gun-Jin Wang, Los Angeles, CA (US)

( * ) Notice: Subject to any disclaimer, the term of this patent is extended or adjusted under 35 U.S.C. 154(b) by 0 days.

(21) Appl. No.: 14/918,463

(22) Filed: Oct. 20, 2015

(65) Prior Publication Data

US 2016/0199311 A1     Jul. 14, 2016

Related U.S. Application Data (63) Continuation-in-part of application No. 14/596,133, filed on Jan. 13, 2015, now abandoned.

(51) Int. Cl.
| | |
|---|---|
| *A61K 39/12* | (2006.01) |
| *A61K 39/135* | (2006.01) |
| *A61K 9/50* | (2006.01) |
| *A61K 35/39* | (2015.01) |
| *A61K 9/48* | (2006.01) |

(52) U.S. Cl.
CPC ............. *A61K 9/5073* (2013.01); *A61K 9/4808* (2013.01); *A61K 9/5036* (2013.01); *A61K 9/5042* (2013.01); *A61K 35/39* (2013.01)

(58) Field of Classification Search
CPC ................... Y10S 514/866; A61K 2039/5254; A61K 2039/552; A61K 39/12; A61K 39/135; C12N 2770/32134; C12N 2770/32151; C12N 7/00
See application file for complete search history.

(56) References Cited

PUBLICATIONS

Anilkumar et al. (Biotechnology and Bioengineering 2001;75(5):581-589).*
Shapiro AMJ. Ricordi C., Hering B.J., et al, International Trial of Edmonton Protocol for Islet Transplantation, New England Journal of Medicine, 2006, 355:1318-30, U.S.A.
Lim, F. & Sun, A.M. Microencapsulated islets as bioartificial endocrine pancreas, Science 210, 1980, 908-910, vol. 210.
Wang T, Lacik I, Brissova M, Anilkumar AV, Prokop A, Hunkeler D, Green R, Shahrokhi K, Powers AC. An encapsulation system for the immunoisolation of pancreatic islets, Nature-Biotechnology, 1997, 15:358-362.
Wang, Taylor, Jamie Adcock, Willem Kühtreiber, Deng Qiang, Kenneth J Salleng, Irina Trenary, Phil Williams, "Successful allotransplantation of encapsulated Islets for diabetic management in Pancreatectomized Canines without the use of Immunosuppression" Transplantation, 2008, vol. 85, 331.

(Continued)

*Primary Examiner* — Ernst V Arnold (57) ABSTRACT

Some embodiments of the present disclosure include an encapsulated islet for treating diabetes. The encapsulated islet may include a semi-permeable capsular membrane having a plurality of layers including an outer immunoprotection layer, a bridging layer, and an inner backbone layer. A continuous fluid-flow manufacturing process may start production of all membrane layers simultaneously, but at different growth rates for different layers. Each layer may have a plurality of pores, wherein the pores increase in size from the immunoprotection layer to the backbone layer, creating the tapered conduits. The semi-permeable capsular membrane may include the following layers, in order from outermost layer to innermost layer: an immunoprotection layer, a bridging layer, and a backbone layer. With proper balancing of membrane thickness and tapered pore size distribution, the encapsulated islets may be configured to offer a improve insulin transport and offer diabetes patients a treatment or functional cure without immunosuppressive drugs.

9 Claims, 5 Drawing Sheets

(56) References Cited

PUBLICATIONS

Soon-Shiong P, Heintz RE, Merideth N, Yao QX, Yao Z, Zheng T, et al. Insulin independence in a Type 1 diabetic patient after encapsulated islet transplantation, Lancet, 1994, 343:950-951.

Trivedi N., Keegan M., Steil G., et al, Islets in alginate macrobeads reverse diabetes despite minimal acute insulin secretory response,Transplantation, 2001, vol. 71, 203-211, U.S.A.

Elghobashi S. On predicting particle-laden turbulent flows, Applied Scientific Research,1994, vol. 52: 309-329, U.S.A.

Herbert E., Turner, J. Stewart "Double-diffusive convection". Journal of Fluid Mechanics, 2008, vol. 106: 299-329. Great Britain.

Gruessner A, Sutherland DE, Gruessner RW: Pancreas transplantation in the United States: 2010, A review. Curr Opin Organ Transplant 15: 93-101.

Ratner, R, Type 2 Diabetes Mellitus: The Grand Overview Diabetic Medicine, 1998, vol. 4, U.S.A.

\* cited by examiner

SEMI-PERMEABLE ENCAPSULATION SYSTEM WITH TAPERED CONDUITS FOR DIABETES REVERSAL

RELATED APPLICATION

This application claims priority to non-provisional patent application U.S. Ser. No. 14/596,133 filed on Jan. 13, 2015, the entire contents of which is herein incorporated by reference.

BACKGROUND

The embodiments described herein relate generally to treatments for endocrine disorders, such as diabetes or hypothyroidism, a neurological disorder, or any other disorder able to be treated with cell therapy, and more particularly, to encapsulated pancreatic islets comprising semi-permeable capsular membrane with tapered conduits.

Diabetes is a difficult disease to manage and treat. Conventionally, there are two acceptable treatment protocols for insulin-dependent diabetes mellitus (IDDDM). Pancreases/pancreatic islet transplantation provides good management of diabetes, but its adoption has been limited by the side effects of immunosuppressive drugs. Insulin injection or use of an insulin pump is less invasive and requires no immunosuppressive drugs, but, for many patients, blood glucose control is inadequate. Neither treatment is satisfactory.

Encapsulated pancreatic islets transplantation has long been considered as one of the more promising alternative treatment protocols for diabetes, wherein a thin (about 0.5 µm) semi-permeable islet encapsulation membrane was assumed to have "uniform pores" that could protect cells from immune attack and, at the same time, would allow the influx of molecules important for cell function/survival and efflux of the other desired cellular products with ease (gatekeeper model). Unfortunately, the "uniform pores" assumption was over simplified and flawed.

Figure 8:
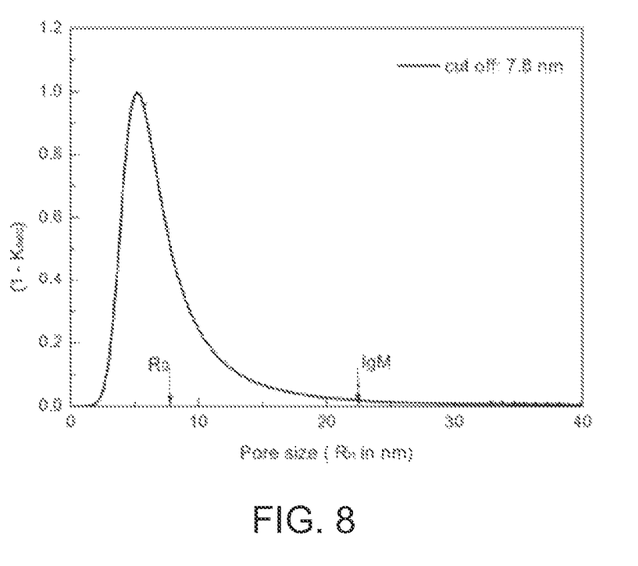
FIG. 8 is a graphical result of capsular membrane layer pore size distribution.

The capsular membrane pore size distribution (PSD) was obtained from the measurements of solute size exclusion coefficients ($K_{SEC}$) with known size of solute molecules. The measured PSD did not agree with the uniform pore size distribution assumption of the gatekeeper model. As shown in FIG. 8, the membrane pore size distribution (PSD—solid line in FIG. 8) was found to have a Gaussian distribution of pore sizes. This was contrary to the gatekeeper model's assumption that there were no pores larger than cutoff ($R_0$) for the immune system to pass through. The thin wall gatekeeper membrane thus could not provide adequate immunoprotection. The erroneous assumption led to a flawed membrane design and unsatisfactory experimental results.

To correct this flaw, a Barrier Model membrane design was developed. The Barrier Model has a thick membrane of about 25 µm with a pore size distribution cutoff (about 90% of pores are smaller than the cutoff) of about 20 nm in diameter. It allows small molecules, such as nutrients and oxygen to enter the membrane with ease. At the same time, the immune system (IgG of about 19 nm and IgM of about 49 nm) would be prevented from breaching the capsule all the way, for it would be stopped or snared by the smaller pores along the way. This is an accumulative effect—the thicker the membrane, the more effective the immunoprotection.

Based on a Statistical Mechanics random walk model, the time, Γ, for an immune system IgG to breach the membrane of a capsule with thickness, D, can be calculated as shown in the following Equation (1):

$$\Gamma \sim 3\tau\left(\frac{D^2}{d^2}\right)\left(\frac{(1-f)}{f}\right) \quad (1)$$

where d is the pore diameter, $D^2/d^2$ represents the total number of random walk steps needed to breach the membrane, τ is the time delay of each random walk step and its value may be extracted from solute size exclusion coefficients measurements, and f is the percentage of pores larger than the immune system.

Equation (1) suggests a Barrier model with about 25 µm in membrane thickness and about 20 nm (150 KDa) in pore size cutoff may be able to keep immune system IgG at bay for up to about 3 years. On the other hand, for a Gatekeeper model with about 0.5 µm membrane thickness and about 12 nm (about 60 KDa) in pore size cutoff, it may be able to keep IgG at bay for about 30 days.

The Barrier model has been tested in canine transplantation experiments, and the results were encouraging. It has normalized fasting blood glucose levels in nine out of nine dogs for up to two hundred and fourteen days with a single transplantation and re-transplantations were equally successful. No immunosuppressant or anti-inflammatory therapy was used or needed.

However, upon closer examination, the thick Barrier model insulin release was found to be wanting. The strength of a Barrier model is also its limitation. It offers good immunoprotection, but inadequate insulin release for two reasons. The first reason is hysteresis, wherein the capsule serves as an insulin reservoir. Like all reservoirs, it resists any sudden changes. The insulin secreted from an encapsulated islet will be held back and diluted before it can be released. This delays the insulin response to glucose challenges. The second reason is viscosity, wherein the capsular membrane is designed to prevent the immune system from entering. So, it stands to reason that the same narrow channels of the capsule may resist insulin from leaving. Together, hysteresis and viscosity effects limit the encapsulated islets' ability to respond to glucose challenges efficiently. The thicker the membrane, or the smaller the pores, the longer the insulin delay and the more limited the insulin release.

The Hagen-Poiseuille equation (Equation (2) below) can be used to estimate the insulin release under non-slip conditions:

$$Q = \left(\frac{\pi d^4}{128}\right)\left(\frac{\Delta p}{D\mu}\right) \quad (2)$$

where Q is the rate of mass flow, d is the channel (pore) diameter, Δp is proportional to the concentration gradient, µ, is viscosity, and D is membrane thickness.

Equations (1) and (2) have shown the dichotomous requirements of immunoprotection and mass transport on a membrane design. If the pores were to increase to improve mass transport, immunoprotection would be compromised. If the membrane thickness was to increase to improve immunoprotection, mass transport would be compromised.

If encapsulated islet transplantation is to be offered as a viable option for diabetic management in humans, encapsulated islet transplantation must be able to keep the patient healthy and encapsulated islets functioning for years, not just for months. Transplantations of encapsulated islets must be able to restore patient's health, and not just provide a short reprieve. None of the current capsular designs could meet this challenge. This was the reason why the encapsulation system has been a "could be" for the diabetes management.

Therefore, what is needed is a new capsular membrane design that can offer islet immunoprotection of a Barrier model and insulin release of a Gatekeeper, thus improving the mass transport without compromising the immunoprotection of encapsulated islets

SUMMARY

Some embodiments of the present disclosure include encapsulated islets for treating diabetes. The encapsulated islet may include a semi-permeable capsular membrane having a plurality of layers including an outer immunoprotection layer, an inner backbone layer, and a bridging layer in between, each layer having a plurality of pores, wherein the pore size distribution cutoffs increase in size from the immunoprotection layer to the backbone layer, creating tapered conduits. These layers are made out of similar polymer compositions of different concentrations that cross-linked well to form a stable membrane. Each of these layers has a plurality of pores; wherein the pores increase in size from the immunoprotection layer to the backbone layer. The tapered design may offer a larger pore size distribution at an interior portion of the membrane for better insulin release. The tapered design may also offer a smaller pore size distribution at an outer surface of the membrane for immunoprotection. The bridging layer may offer a gradual change in pore size distribution to match the pores of both ends for continuity. Thus, the tapered conduits may offer improved mass transport without compromising the immunoprotection.

BRIEF DESCRIPTION OF THE FIGURES

The detailed description of some embodiments of the invention is made below with reference to the accompanying figures, wherein like numerals represent corresponding parts of the figures.

DETAILED DESCRIPTION OF CERTAIN EMBODIMENTS

In the following detailed description of the invention, numerous details, examples, and embodiments of the invention are described. However, it will be clear and apparent to one skilled in the art that the invention is not limited to the embodiments set forth and that the invention can be adapted for any of several applications.

The device of the present disclosure may be used to treat diabetes, allowing the insulin to be sufficiently released into the body while also sufficiently blocking the immune response and may comprise the following elements. This list of possible constituent elements is intended to be exemplary only, and it is not intended that this list be used to limit the encapsulated islets of the present application to just these elements. Persons having ordinary skill in the art relevant to the present disclosure may understand there to be equivalent elements that may be substituted within the present disclosure without changing the essential function or operation of the device.

1. Encapsulated Islet
2. Semi-Permeable Capsular Membrane with Tapered Conduits

The various elements of the encapsulated islet of the present disclosure may be related in the following exemplary fashion. It is not intended to limit the scope or nature of the relationships between the various elements and the following examples are presented as illustrative examples only.

Figure 1:
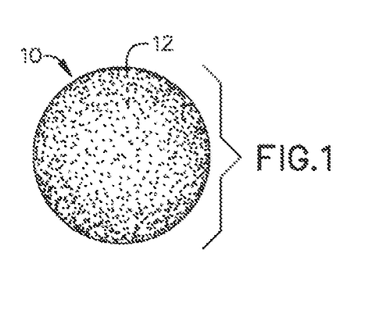
FIG. 1 is a perspective view of one embodiment of the present disclosure.
Figure 2:
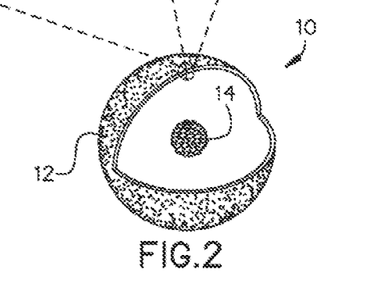
FIG. 2 is a cutaway/detail perspective view of one embodiment of the present disclosure.
Figure 3:
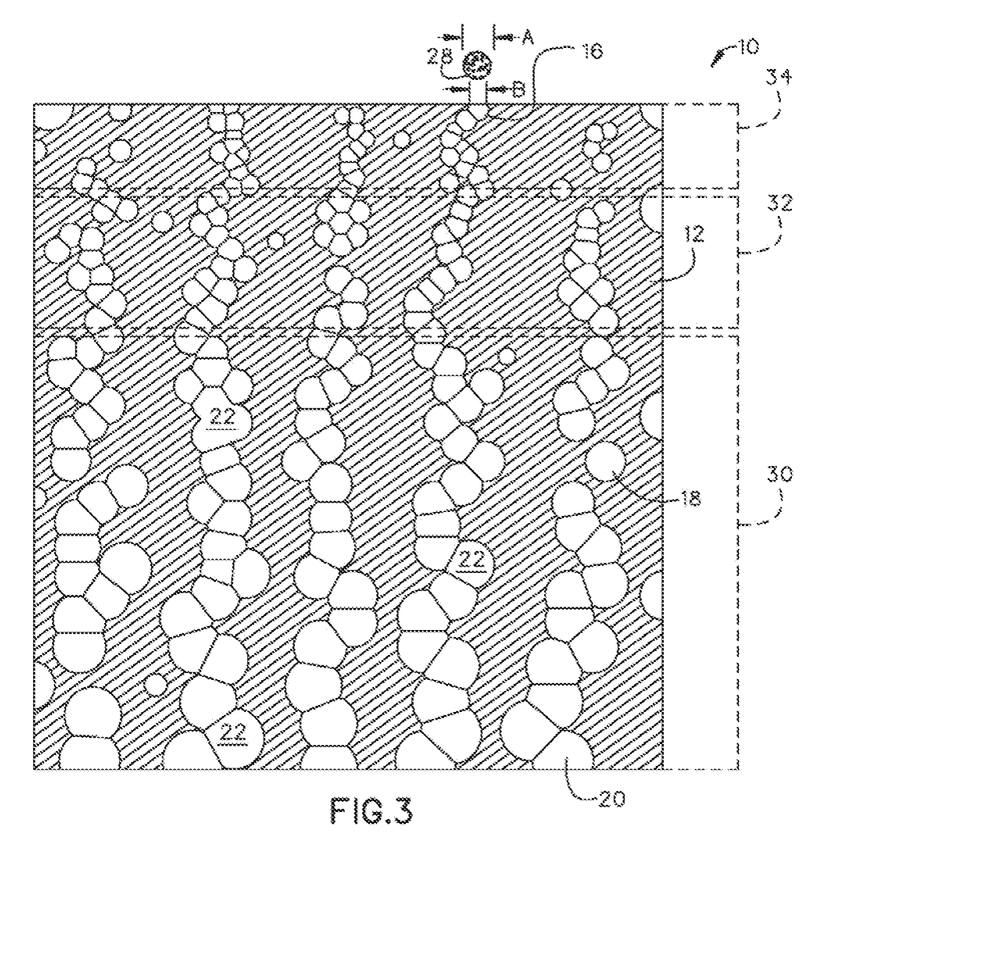
FIG. 3 is a section detail view of one embodiment of the present disclosure.

By way of example, and referring to FIGS. 1-3, some embodiments of the present invention comprise an encapsulated islet 10 comprising a semi-permeable capsular membrane 12 having tapered conduits 22, wherein the conduits 22 are configured to sufficiently release insulin into the body while simultaneously blocking the natural immune response. Each layer of different concentrations of similar polymer compositions may have different pore size distribution cutoffs. By design, the polymer concentration may decrease toward an interior of the membrane 12, wherein the pore size distribution cutoffs may decrease toward an exterior of the membrane 12, as shown in FIGS. 1-3. This capsular membrane 12 with a tapered pore size distribution design may be able to improve mass transport without jeopardizing immunoprotection.

In embodiments, the semi-capsular membrane 12 may comprise a plurality of layers, wherein each membrane, from an immunoprotection layer 34 to a bridging layer 32 to a backbone layer 30, comprises increasingly larger pores, resulting in an overall structure having tapered conduits 22. Specifically, by adjusting the concentrations of polymer constituents and reaction times, layers with different pore size combinations may be formed. Thus, a membrane with different tapered conduits may be formed.

Figure 4:
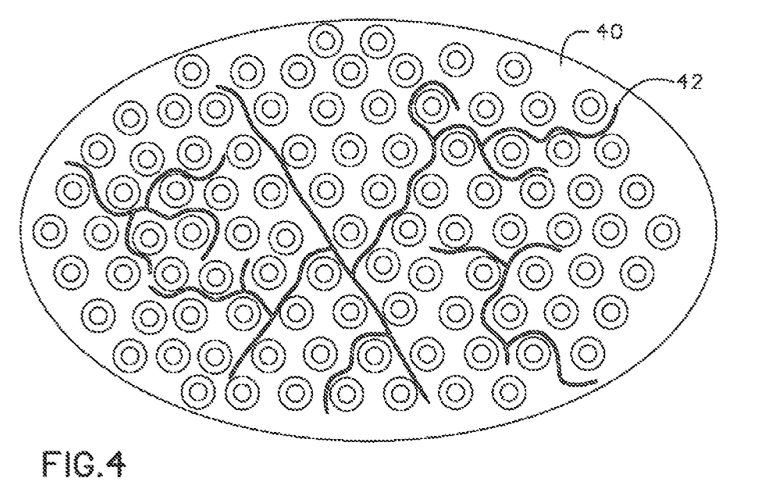
FIG. 4 is a section view of one embodiment of the present disclosure shown in use.

As shown in FIG. 3, some embodiments of the semi-permeable capsular membrane 12 may comprise three layers, wherein the outermost layer (Layer 3) comprises an immunoprotection layer 34, the central layer (Layer 2) comprises a bridging layer 32, and the innermost layer (Layer 1) comprises a backbone layer 30, wherein the layers comprise pores that increase in size from an outermost layer to an innermost layer, allowing increased insulin release while simultaneously providing protection against immune systems. In embodiments, each layer may comprise different concentrations of similar polymer compositions for different pore size distributions. The layers with similar polymer compositions may be cross-linked to form a stable, semi-permeable capsular membrane 12. In embodiments and as shown in FIG. 4, the encapsulated islet 10 may further comprise an outermost ablation layer, ablation beads, or ablation patches.

The ablation layer, beads, or patches may protect the islets from the post-transplant immune surge by shedding patch material continuously and may comprise a polymer comprising $CaCl_2$ and sodium alginate (SA). The ablation layer, beads, or patches may have pores with a diameter of about 30 nm or larger.

The immunoprotection layer 34 may comprise a thin polymer membrane comprising polymethylene-co-guanidine (PMCG), cellulose sulfate (CS), poly L-lysine (PLL), and sodium alginate (SA). Thus, the immunoprotection layer 34 may comprise a polymer membrane of PMCG-CS/PLL-SA. The immunoprotection layer 34 may comprise a plurality of immunoprotection pores 16 with a pore size distribution cutoff about 15 nm in diameter and about 0.5 μm in thickness.

The bridging layer 32 may comprise a membrane comprising PMCG, CS, PLL, SA, and calcium chloride ($CaCl_2$). Thus, the bridging layer 32 may comprise a polymer membrane of PMCG-CS/PLL-SA-$CaCl_2$. The bridging layer 32 may comprise a plurality of bridging pores 18 having a pore size distribution cutoff between about 20 nm and about 15 nm in diameter and a thickness of about 0.5 μm to bridge between the backbone layer 30 and the immunoprotection layer 34. The bridging layer 32 may be configured to ease the transition and improve the mass transport between the outer, immunoprotection layer 34 and the inner, backbone layer 30.

The backbone layer 30 may be the innermost layer and may comprise a polymer membrane comprising PMCG, CS/$CaCl_2$, and SA. Thus, the backbone layer 30 may comprise a polymer membrane of PMCG-CS/SA-$CaCl_2$. The backbone layer 30 having a thickness of, for example, about 25 μm, may comprise a plurality of backbone pores 20 having pore size distribution cutoffs gradually decreasing from about 30 nm to about 20 nm in diameter.

In one particular embodiment, the backbone layer 30 may have a thickness of about 25 μm and may comprise backbone pores 20 with pore size distribution cutoffs gradually decreasing from about 30 nm in diameter to about 20 nm in diameter. The bridging layer 32 may have a thickness of about 0.5 μm and may comprise bridging pores 18 with a pore size distribution cutoff gradually decreasing from about 20 nm to about 15 nm in diameter, and the immunoprotection layer 34 may have a thickness of about 0.5 μm and may comprise immunoprotection pores 16 with a pore size distribution cutoff of about 15 nm in diameter. Interconnecting these pores of the different layers together form the tapered conduits 22.

The tapered geometry of the conduits 22 with the larger inlet at the inner surface may result in increased insulin release while simultaneously maintaining good immunoprotection with small pores at the exterior surface, as shown in FIGS. 2 and 3. The glucose inflow and insulin outflow may be explicitly linked, wherein they are two legs of a double concentration gradient diffusion driven convection. Convective flow with enlarged tapered conduit diameters may improve the mass transport in both flow directions. Thus, both glucose uptake and insulin release are increased. Together, they may improve encapsulated islet performance and diabetic management.

Materials and Methods

Example

To improve transplantation performance, a new encapsulation system with tapered conduits was developed to improve mass transport without comprising the immunoprotection. This design offers a membrane with gradually decreasing pore sizes from an inner surface to an outer surface, thus mimicking the function of a nozzle. A combination of polyanion [alginate (Alg) and cellulose sulfate (CS)] and polycation [polymethylene-co-guanidine (PMCG), poly L-lysine (PLL), and $CaCl_2$] was found most promising.

Capsule fabrication started by introducing polyanion [Alg-CS droplets (about 0.5% to about 3%)] into a polycation stream [PMCG (about 0.6% to about 2%), $CaCl_2$ (about 0.8% to about 2.5%), and PLL (about 0.2% to about 0.1%)]. $CaCl_2$, being the smallest molecule, entered the Alg-CS matrix first to initiate the jelling process of Ca-CS/Ca-Alg. PMCG, being a larger molecule, followed behind and bonded with CS preferentially to form a PMCG-CS/Ca-Alg membrane layer. Ca and PMCG molecules continued to diffuse inward to form a thicker membrane. Meanwhile, PLL with the largest molecular weight (about a few tens kDa) trailed further behind and formed a thin, stable PMCG-CS/PLL-Alg membrane layer at the outer surface of the capsule with pores of about 16 nm in diameter.

The small pores of the PMCG-CS/PLL-Alg layer were less permeable to PMCG than to Ca molecules. Decreased PMCG concentration favored membrane formation with larger pore size distribution cutoff. As the PMCG-CS/PLL-Alg membrane thickened, the PMCG concentration decreased, and the PMCG-CS/Ca-Alg membrane's pore size distribution increased, forming a membrane with tapered conduits with wider ends positioned at an inner surface and narrower ends positioned at the outer surface.

This continuous fluid-flow membrane manufacturing process starts all membrane layers simultaneously, but different layers have different growth rates for different polymer mobility. This continuous membrane growth process creates transport conduits with no discontinuity between layers.

By measuring capsular parameters at the different stages of membrane formation, overall tapered conduit membrane construction may be approximated:

(1) The jelled Ca-Cs/Ca-Alg matrix offers a framed structure for the membrane to form. The matrix has a pore size distribution of about 30 nm, and the polymer sphere is about 800 μm in diameter. It protects the islets during the encapsulation process. Post encapsulation, the jelled Ca-Cs/Ca-Alg matrix may be gradually liquefied in a sodium rich environment, leaving behind a spherical capsule.

(2) The inner surface of the capsule may be a thick membrane layer of PMCG-CS/CA-Alg. It has tapered pore size distribution cutoffs from about 30 nm to about 20 nm and a membrane thickness of about 25 μm. The tapered channels may improve mass transport, and the thick layer may improve the immunoprotection. It is the primary backbone layer of the capsule.

(3) The outer surface of the capsule may be a thin polymer layer of PMCG-CS/PLL-Alg. It has a pore size distribution cutoff of about 15 nm in diameter and a membrane thickness of less than about 0.5 μm. It is the immunoprotection layer of the capsule.

(4) In between the backbone and immunoprotection layers, there is a thin bridging layer of PMCG-CS/CA-Alg-PLL providing porosity continuity for mass transport. It has tapered pore size distribution cutoffs of from about 20 nm to about 15 nm in diameter and a membrane thickness of about 0.5 μm.

Experiments

NHP Transplantation Experiments

A non-human primate (NHP) model was chosen to test the new tapered capsule model as a precursor to human clinical trial for the following advantages: (1) NHPs and humans share about 90% of DNA, (2) humans and NHPs are both bipedal, (3) a NHP is a difficult diabetic patient to manage, because it needs 10 times more insulin/kg than a human to manage its diabetes, (4) a NHP is temperamental and fragile, not enduring stress or treatment well, making a NHP a much more challenging model than a human for islet transplantation. Therefore, if the tapered conduit encapsulation system functions well in a NHP model, it will likely function well in humans.

Encapsulated islets were surgically placed at a desired intraperitoneal or subcutaneous site of a diabetic animal. Upon aesthetic recovery, the animals were transferred to their cages and provided with their daily food ration.

Immunoprotection Efficacy of Capsular Membrane with Tapered Conduits

Figure 5:
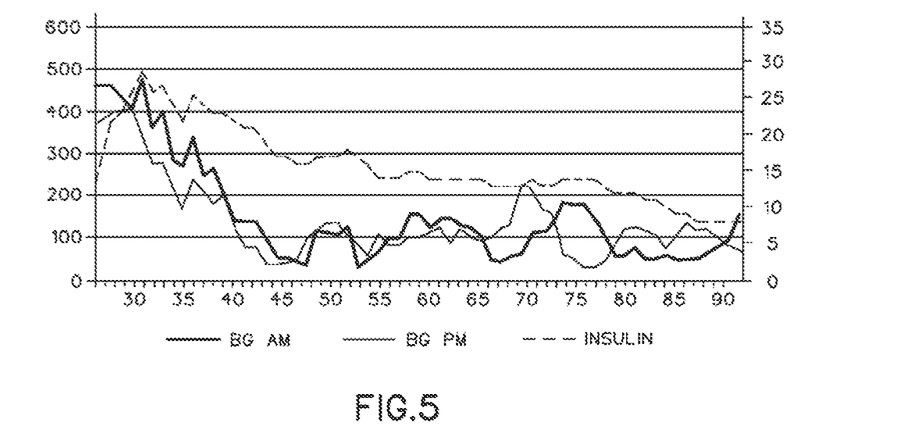
FIG. 5 is a graphical result of NHP 4510 transplantation experiment.

The objective of this NHP xeno-transplantation experiment (human donors) was to study the immunoprotection efficacy of the tapered conduit encapsulation system. NHP 4510 (5 kg in body weight BW) received two transplants with 6 capsule patches each containing a total of about 1,350,000 encapsulated human islets. These capsules were transplanted on momentum and a subcutaneous fat pad. The capsules exceeded 9 times of islet packing density needed for human allotransplantation. About 3 weeks after the incubation period, the exogenous insulin requirement for NHP 4510 started to drop. It gradually fell from 25-30 units/day to 7-10 units/day in 90 days with good glycemic control, as shown in FIG. 5. This suggested the tapered conduit capsule design was able to provide good immunoprotection in an extremely challenged xenotransplantation environment with no immunosuppressive or anti-inflammatory drugs.

Mass Transport Efficiency of Capsular System with Tapered Conduits

The objective of this NHP allo-transplantation experiment was to study the mass transport efficiency of the tapered conduit encapsulation system. At the start of the glucose challenge, the encapsulated islet insulin production may be low, and the diffusive flow may be slow. The momentum exchange between insulin and extracellular fluid may be considered negligible. Insulin hormone transport mechanism in a tapered conduit may be described as a "particle laden two-phase diffusive fluid flow." As the glucose challenge continues, insulin production may increase, and the dynamic interaction between the insulin, which is about 4 nm in diameter, and the extracellular fluid in a tapered channel having a diameter of about 16 nm may no longer be neglected.

The flow mechanism may gradually change into a "two-way momentum coupling." The insulin outward flow in a tapered conduit may accelerate on its way out of the capsule with extracellular fluid. The oxygen and glucose inward diffusive flow may be enhanced by the extracellular fluid return flow. This closed loop fluid flow may feed on each other and create the "Double-Diffusive Convection." This convective flow may increase the mass transport efficiency in both directions, increasing glucose, nutrient, and oxygen uptake and speeding up insulin release.

Figure 6:
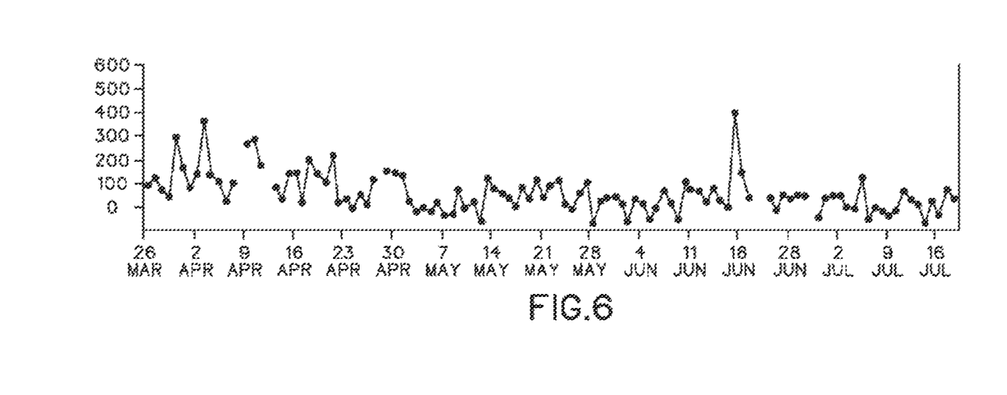
FIG. 6 is a graphical result of NHP 3912 transplantation experiment.

As shown in FIG. 6, the tapered conduit capsules with 180,000 IEQ encapsulated islets secreted about 5 units of insulin. In comparison, barrier model capsules with 710,000 IEQ encapsulated islets secreted about 14 units of insulin in a canine transplantation experiment with non-tapered pores of about 20 nm in diameter. Thus, the tapered conduit capsular design increased insulin output per transplanted islet by a factor of 50%.

Diabetes Management of Capsular Membranes with Tapered Conduits

Figure 7:
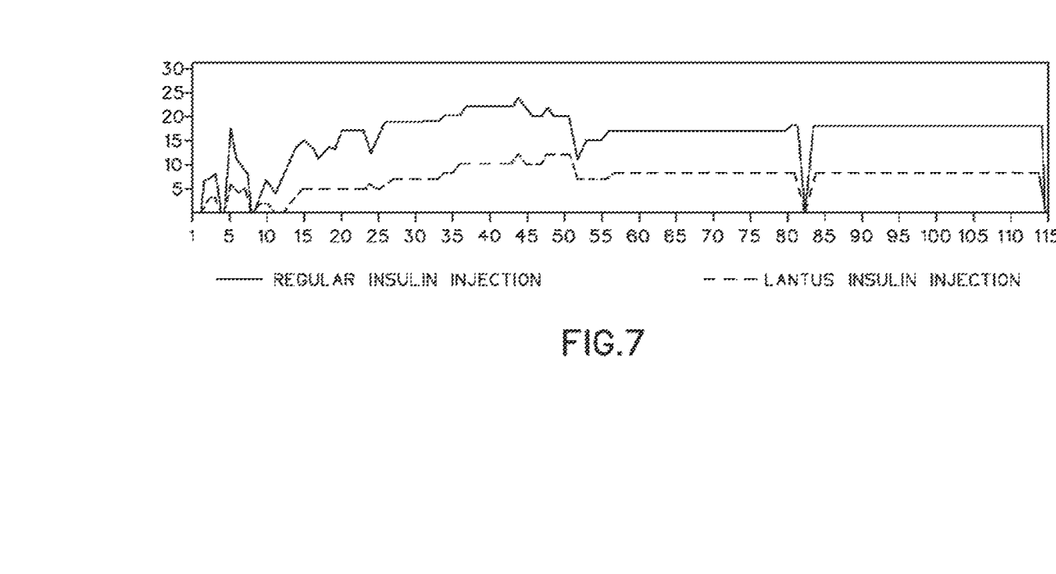
FIG. 7 is a graphical result of NHP 3912 transplantation experiment.

The objective of this NGP allo-transplantation experiment was to study the diabetes management performance of the tapered conduit encapsulation system. NHP 3912 (5 kg in BW) received a sub-therapeutic dosage of 180,000 encapsulated NHP islets (⅙ of a full dosage). Supplemental Lantus and regular insulin were provided for basal and meal requirements. After a 3-week incubation period, encapsulated NHP islets were able to start waning off the corrective insulin bolus. Six weeks post transplantation, these encapsulated islets (without correction boluses) were able to maintain good glycemic control by reducing BG fluctuations within normoglycemic ranges, as shown in FIGS. 6 and 7.

Most diabetic patients experienced progressive deterioration of their diabetic management; their islets seem to burn out gradually, and insulin injection or islet re-transplantation was needed. In NHP 3912, the animal has shown steady diabetic improvement with more robust islet functions after the incubation period, as shown in Table 1 below:

|  | Days 0-32 | Days 33-65 | Days 66-98 | Days 99-119 |
|---|---|---|---|---|
| Plasma Glucose | 220 ± 74 | 150 ± 56 | 127 ± 42 | 102 ± 37 |
| HbA1c | 9.3 | 6.85 | 6.05 | 5.2 |

The table suggests tapered conduits could provide improvements on islet health and functional longevity. Moreover, tapered conduit capsules may improve insulin transport without adversely impacting immunoprotection. Specifically, the data demonstrates that the transplanted encapsulated islets are healthy and recovering their full function. Thus, encapsulated islet transplantation may be able to offer type I diabetic patients a functional cure without immunosuppressive drugs.

Use of the encapsulated islets of the present invention, wherein the islet comprise a semi-permeable membrane comprising tapered conduits, may provide a functional cure for diabetes.

Potential Benefits to Type I Diabetic Patients

For type I diabetic patients, tapered conduit capsules may be able to keep the immune system at bay for about 2-3 years per transplant. Specifically, the tapered conduit encapsulation system may offer type I diabetic patients two possible transplantation protocols.

Diabetes Reversal:

For diabetic patients with advanced disease, a full dosage of encapsulated islets (about 1,200,000 IEQ) with tapered conduits may provide an insulin-independent functional cure without immunosuppressive drugs. This may offer patients with advanced disease a much more compassionate diabetic management protocol. An average sized human may have enough space to accept about 3 million or more encapsulated islets. This suggests at least one re-transplantation may be possible to extend the length of diabetic management.

Diabetes Management:

For healthy type I diabetic patients, transplantations of a sub-therapeutic dosage of encapsulated islets (about 300,000 IEQ) may eliminate the need of a correction bolus. Together with steady dosages of basal and meal boluses, this protocol may offer patients a better diabetic management and may free them from worrying about their blood glucose constantly. Moreover, possible multiple re-transplantations may offer patients a lifetime of improved diabetic management.

Regardless of which transplant protocol patients choose in the future, the tapered conduit encapsulation system may offer patients a better diabetic management without immunosuppressive drugs, as well as the convenience of significantly less daily testing or adjusting their daily insulin dosage, thus resulting in less anxiety and uncertainty.

Potential Benefits to Type II Diabetic Patients

Islet encapsulation was developed to benefit type I diabetic patients. However, type II diabetic patients may benefit from sub-therapeutic encapsulated islet transplantation in greater numbers. There are 25.8 million children and adults in the United States—8.3% of the total population—with diabetes, and 90% of them are type II diabetics. Most patients with type II diabetes experience progressive loss of islet function. Their overworked islets seem to burn out, and these patients eventually require insulin injections to manage their diabetes.

For healthy type II diabetic patients, the lifelong immunosuppressive drug requirement has precluded them from participating in islet transplantation based on the benefit/risk criteria. However, the tapered conduit capsule transplantation protocol without immunosuppressive drugs may tip the scale the other way. Thus, many type II diabetic patients may benefit from sub-therapeutic islet transplantations by replacing damaged islets and keeping diabetes under control, which may arrest the progression of diabetes before it starts to ravage the patient's body and rob them of their quality of life.

Persons of ordinary skill in the art may appreciate that numerous design configurations may be possible to enjoy the functional benefits of the inventive systems. Thus, given the wide variety of configurations and arrangements of embodiments of the present invention the scope of the invention is reflected by the breadth of the claims below rather than narrowed by the embodiments described above.

What is claimed is:

1. An encapsulated islet for treating diabetes, the encapsulated islet comprising:
    a semi-permeable capsular membrane comprising tapered conduits, wherein:
    the semi-permeable capsular membrane comprises a plurality of layers including:
        an outer immunoprotection layer comprising a plurality of immunoprotection pores having a pore size distribution cutoff of about 15 nm in diameter,
        a bridging layer comprising a plurality of bridging pores having a size distribution cutoff gradually decreasing from about 20 nm to about 15 nm in diameter, and
        an inner backbone layer comprises a plurality of backbone pores having a size distribution cutoff gradually decreasing from about 30 nm to about 20 nm in diameter;
    the pores increase in size from the immunoprotection layer to the backbone layer, creating the tapered conduits; and
    the layers are made of similar polymer compositions configured to cross-link with one another to form a stable membrane.

2. The encapsulated islet of claim 1, further comprising an outermost ablation layer, such that an order of the layers is the ablation layer, the immunoprotection layer, the bridging layer, and the backbone layer from outermost to innermost layer.

3. The encapsulated islet of claim 2, wherein the ablation layer comprises a polymer comprising $CaCl_2$ and sodium alginate (SA).

4. The encapsulated islet of claim 1, wherein:
    the immunoprotection layer comprises a polymer membrane comprising polymethylene-co-guanidine (PMCG)-cellulose sulfate (CS)/poly L-lysine (PLL), and sodium alginate (SA).

5. The encapsulated islet of claim 1, wherein:
    the bridging layer comprises a polymer membrane of $PMCG-CS/PLL-SA-CaCl_2$.

6. The encapsulated islet of claim 1, wherein:
    the backbone layer comprises a polymer membrane of $PMCG-CS/SA-CaCl_2$.

7. The encapsulated islet of claim 1, wherein:
    the immunoprotection layer has a thickness of about 0.5 μm;
    the bridging layer has a thickness of less than or equal to about 0.5 μm; and
    the backbone layer has a thickness of about 25 μm.

8. A system for treating diabetes, the system comprising:
    a capsule configured to be surgically placed at a desired intraperitoneal or subcutaneous site of a diabetic patient; and
    a plurality of encapsulated islets held in place by the capsule, each encapsulated islet comprising:
        a semi-permeable capsular membrane comprising tapered conduits, wherein:
    the semi-permeable capsular membrane comprises a plurality of layers including:
        an outer immunoprotection layer comprising a plurality of immunoprotection pores having a pore size distribution cutoff of about 15 nm in diameter,
        a bridging layer comprising a plurality of bridging pores having a size distribution cutoff gradually decreasing from about 20 nm to about 15 nm in diameter, and
        an inner backbone layer comprises a plurality of backbone pores having a size distribution cutoff gradually decreasing from about 30 nm to about 20 nm in diameter; and
    the pores increase in size from the immunoprotection layer to the backbone layer, creating the tapered conduits.

9. The system of claim 8, wherein:
    the immunoprotection layer comprises a polymer membrane comprising polymethylene-co-guanidine (PMCG)-cellulose sulfate (CS)/poly L-lysine (PLL), and sodium alginate (SA);
    the bridging layer is cross-linked to the immunoprotection layer and comprises a polymer membrane of $PMCG-CS/PLL-SA-CaCl_2$, and
    the backbone layer is cross-linked to the bridging layer and comprises a polymer membrane of $PMCG-CS/SA-CaCl_2$.

* * * * *